United States Patent [19]
Romette et al.

[11] Patent Number: 4,780,191
[45] Date of Patent: Oct. 25, 1988

[54] L-GLUTAMINE SENSOR

[75] Inventors: Jean L. Romette, Belmont; Charles L. Cooney, Brookline, both of Mass.

[73] Assignee: Massachusetts Institute of Technology, Cambridge, Mass.

[21] Appl. No.: 67,641

[22] Filed: Jun. 26, 1987

[51] Int. Cl.$^4$ ............................................. G01N 27/30
[52] U.S. Cl. ................................... 204/403; 204/1 T; 435/16; 435/25; 435/291; 435/817
[58] Field of Search ................ 204/1 E, 403, 415; 435/291, 4, 16, 25, 817

[56] References Cited

U.S. PATENT DOCUMENTS

| | | | |
|---|---|---|---|
| 4,024,021 | 5/1977 | Stavropoulos et al. | 435/25 X |
| 4,353,983 | 10/1982 | Siddiqi | 435/25 X |
| 4,614,714 | 9/1986 | Kusakabe et al. | 435/25 |
| 4,655,880 | 4/1987 | Liu | 204/1 T |

FOREIGN PATENT DOCUMENTS 248605 12/1987 German Democratic Rep. .... 435/4

OTHER PUBLICATIONS

M. A. Arnold et al., Anal. Chem., vol. 52, pp. 1170–1174, (1980).
G. A. Rechnitz et al., Nature (London), vol. 278 pp. 466–467 (1979).
G. G. Guilbault et al., Anal. Chim. Acta, vol. 56, pp. 333–338 (1971).
J. L. Romette et al. Clin. Chim. Acta, vol 95, pp. 249–253 (1979).
H. Kusakabe et al., Agric. Biol. Chem., vol 48(5) pp. 1357–1358 (1984).

Primary Examiner—G. L. Kaplan

[57] ABSTRACT

Apparatus for measuring L-glutamine in a liquid sample includes a membrane on which are immobilized the enzymes glutaminase and glutamate oxidase, whereby any said L-glutamine in the sample is acted upon by the glutaminase to form glutamic acid, the glutamic acid being acted upon by the glutamate oxidase to form an enzymatic reaction product, the membrane being operatively associated with a sensor capable of sensing the enzymatic reaction product or a compound or element consumed or liberated in the formation or degradation thereof.

4 Claims, 5 Drawing Sheets

L-GLUTAMINE SENSOR

BACKGROUND OF THE INVENTION

This invention relates to monitoring and controlling of cell culture conditions.

Mammalian cells are cultured in vitro for their production of biomolecules unavailable, or available with greater difficulty, from other sources, including for example glycosylated proteins having therapeutic value, such as tissue plasminogen activator.

There is an increasing demand for analytical methods allowing on line control of mammalian cell cultures. A typical mammalian cell culture medium generally includes bovine serum, a mixture of amino acids (including ten essential amino acids), vitamins, growth factors, and minerals. The essential amino acid glutamine provides a particularly useful energy source for mammalian cells in culture, because metabolism of glutamine produces no lactic acid. Glutamine is thus typically provided in cell culture media in excess of requirements for it as an essential amino acid. When glutamine is present in too great an excess, however, ammonia is produced by the culture, and ammonia inhibits growth and production by the cells.

Available techniques for measuring glutamine concentrations in mammalian cell culture include high performance liquid chromatography (HPLC) or colorimetric or fluorimetric methods, which may require addition of reagents such as chromogenic substances to the medium.

One approach to direct, on line measurement of amino acids in liquid samples is to use a bioselective membrane electrode. M. A. Arnold et al., *Anal. Chem.*, 1980, vol. 52, pages 1170-74, compared the performance of four different glutamine sensors, all dependent upon biocatalytic deamination of glutamine to produce glutamate and ammonia and measurement of the resulting ammonia using a commercially available ammonia gas sensing potentiometric electrode. One of the four sensors was an immobilized isolated enzyme electrode in which a suspension of glutaminase (E.C. 3.5.1.2) was directly placed on the gas permeable membrane of the ammonia sensor, and held in place with a dialysis membrane, as described in G. A. Rechnitz et al., 1979, *Nature* (London), vol. 278, pages 466-67; and G. G. Guilbault et al., 1971, *Anal. Clim. Acta*, vol. 56, pages 333-38.

SUMMARY OF THE INVENTION

In general, the invention features apparatus for measuring L-glutamine in a liquid sample, which includes a membrane on which are immobilized the enzymes glutaminase and glutamate oxidase, whereby any L-glutamine in the sample is acted upon by the glutaminase to form glutamic acid, which is acted upon by the glutamate oxidase to form an enzymatic reaction product, the membrane being operatively associated with a sensor capable of sensing the enzymatic reaction product or a compound or element consumed or liberated in the formation or degradation of the enzymatic reaction product.

In preferred embodiments, the glutaminase and the glutamine oxidase are immobilized in an inert protein matrix; the sensor measures dissolved oxygen and the membrane is oxygen permeable; and the inert protein matrix is gelatin.

The sensor requires no reagents for use, and it is inexpensive and compact and readily adapted to on-line real-time use in nearly any cell culturing system. The sensor is ideal for feed-back control of a flow-through system: whenever the sensor indicates that glutamine concentrations are suboptimally high or low, an adjustment may be made (either manually or automatically) in the culture medium (by, e.g., differential dilution of media flowing into the fermentor) in a time scale (about two minutes) much smaller than the relevant time scale for mammalian cell culture systems (about an hour).

The enzyme electrode of the invention can be used to measure glutamine concentration in complex cell growth medium; thus it is suitable for on-line real time process control of mammalian cell culture. The sensor is highly sensitive and very stable, both in storage and in operation, and its specificity and fast response make it suitable for use in automation.

Other features and advantages of the invention will be apparent from the following description of the preferred embodiment, and from the claims.

DESCRIPTION OF THE PREFERRED EMBODIMENT

We first briefly describe the drawings.

Drawings

Structure

Figure 1:
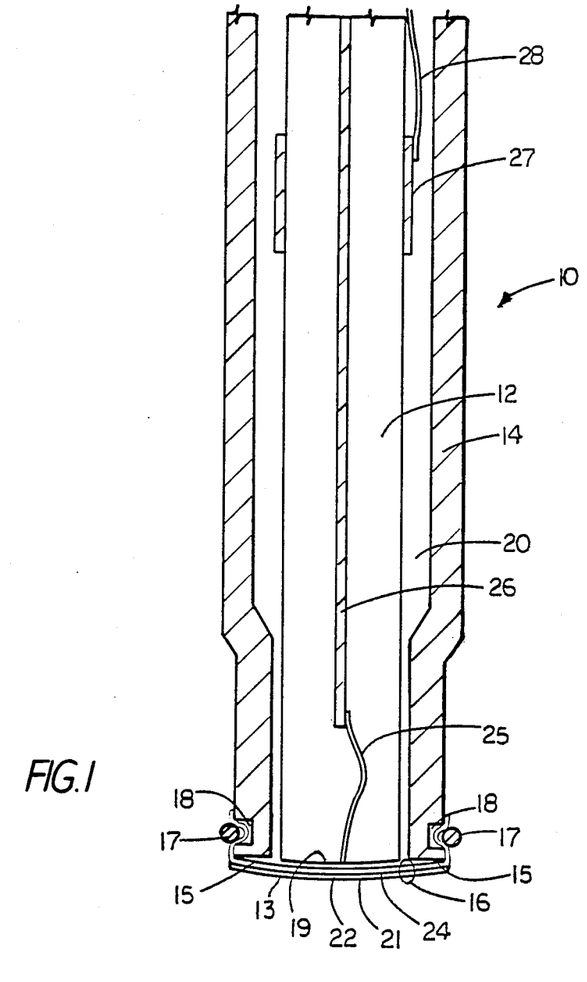
FIG. 1 is a somewhat diagrammatic sectional view of part of an L-glutamine sensor of the invention.

Referring to FIG. 1, glutamine sensor 10 is a standard Clark-type electrode which we have equipped with bioselective membrane 16, which includes inner gas selective membrane 24, which contacts electrolyte film 21, and outer enzyme gelatin support layer 22, in which the enzymes glutaminase and glutamate oxidase are immobilized. The Clark-type electrode in sensor 10 allows amperometric measurement of the dissolved oxygen partial pressure ("pO$_2$") at gas selective membrane 24; such electrodes are commercially available (e.g., Radiometer, Copenhagen, Denmark, model E 5046), and their structure is generally familiar to one skilled in the art. The electrode includes pO$_2$ sensing electrode body 12 enclosed within electrode jacket 14. Bioselective membrane 16 is drawn over end 15 of electrode jacket 14 and tip 13 of sensing electrode body 12, and held in place in a customary manner by O-ring 17 in annular groove 18. Occupying space 20 between electrode jacket 14 and sensor electrode body 12, and retained by bioselective membrane 16, is an electrolyte, preferably KCl in phosphate buffer, made by mixing 1.04 g KCl, 10.25 g B-basic phosphate (Na$_2$HPO$_4$·12-H$_2$O), and 2.6 g NaH$_2$PO$_4$ in 100 ml water. The electrolyte is drawn into a thin film 21 between tip 13 of electrode body 12 and inner surface 19 of bioselective membrane 16. Sensing electrode body 12 contains platinum wire cathode 25, connected to a pO$_2$ meter (not shown) through cathode lead 26 and making contact with electrolyte film 21 at tip 13 of electrode body 12; and Ag-/AgCl anode 27, connected to the pO$_2$ meter by anode lead 28 and making contact with the surrounding electrolyte in space 20 between electrode jacket 14 and sensor electrode body 12.

Manufacture

Bioselective membrane 16 is constructed using the following starting materials. Inner gas selective layer 24 is a suitably gas permeable film, preferably a polypropylene film 6 μm thick (Bollore, Paris, France). Enzyme gelatin support layer 22 is a mixture of glutamate oxidase (from Streptomyces species X-119-6 (Yamasa Shoyu, Choschi Shiba, Japan)), and glutaminase (grade V from *Escherichia coli* (Sigma Co., St. Louis, MO)), in an inert protein matrix made up of hardened and insolubilized gelatin from bone with a hardness characteristic of 250 blooms (Rousselot Chemical, Paris, France), prepared generally as described by J. L. Romette et al., 1979, *Clin. Chim. Acta*, vol. 95, pages 249–253. All other chemicals are reagent grade.

A bioselective membrane 16 having good mechanical properties is made as follows. A 5% gelatin solution is prepared by dissolving the gelatin in phosphate buffer (0.05M, pH 6.8) for 20 min at 60° C. After the gelatin dissolves, 0.150 mg/ml of glutaminase and 0.84 mg/ml of glutamate oxidase are added to form a gelatin-enzyme mixture; these proportions correspond to a mixture having an activity of 10 international units ("IU") of each enzyme per ml. The selective gas membrane is coated with a layer of gelatin-enzyme mixture by pouring 1 ml of the mixture onto a 35 cm$^2$ area of polypropylene film fixed on a levelled glass plate. The resulting enzyme-gelatin support layer is dried at 25° C. for 2 hours under air flow conditions and then the selective gas membrane with the enzyme-gelatin support layer is immersed in a 1.25% glutaraldehyde solution in phosphate buffer (0.05M, pH 6.8) for 3 minutes to insolubilize the enzyme-gelatin support layer. The enzyme-gelatin support is "insolubilized", as that term is used herein, when the enzymes are bound within the gelatin and the gelatin is substantially insoluble in the liquid samples to be assayed for L-glutamine. This prepared bioselective membrane is then drawn over the tip 13 of sensing electrode body 12 and end 15 of electrode jacket 14 and held in place with an O-ring 17 as described above.

One skilled in the art will appreciate that a satisfactory bioselective membrane may be made using methods differing in particulars from the protocol described above, as described, for example, in J.-C. Quennesson et al., French Patent No. 77 15616.

Operation

To use the L-glutamine sensor, the sample whose glutamine concentration is to be determined is allowed to contact the outer surface (39 in FIG. 2) of the enzyme-gelatin support layer 22. As solutes in the sample, including L-glutamine, diffuse into the inert protein matrix layer, the L-glutamine reaches the glutaminase. The glutaminase (E.C. 3.5.1.2), according to the reaction described by S. C. Hartman, 1968, *J. Biol. Chem.*, vol. 243, pages 853–63, catalyzes the transfer of the amide nitrogen of glutamine, requiring a mole each of water and glutamine to produce a mole each of glutamic acid and ammonia. This may be shown as follows:

glutamine + H$_2$O $\xrightarrow{\text{Glutaminase}}$ L-glutamate + ammonia

By further diffusion, the glutamic acid reaches the glutamate oxidase. The glutamate oxidase (extracted from Streptomyces species X-119-6, as described by Kusakabe et al., 1983, *Agric. Biol. Chem.*, vol. 47, pages 179–82, and H. Kusakabe et al., 1984, *Agric. Biol. Chem.* vol. 48, pages 181–84) oxidizes the glutamic acid, requiring a mole each of water and glutamic acid to produce a mole each of ammonia and α-ketoglutarate; this is a flavin-coupled ping pong reaction, in which a mole of FAD is reduced to FADH$_2$ to drive the oxidation of glutamic acid, and O$_2$ is in turn consumed mole-for-mole in restoring FADH$_2$ to FAD, producing a mole of H$_2$O$_2$. This may be shown as follows:

Thus, there is a direct stoichiometric relationship between glutamine concentration in the sample and the rate of O$_2$ depletion in the enzyme-protein matrix layer. The O$_2$ depletion is measured by the O$_2$-sensing electrode.

Characteristics of the enzymes are shown in Table 1.

TABLE 1

Enzyme Characteristics

| Enzyme | Source | $K_m$ | pH optimum | $K_{cat}$ sec$^{-1}$ |
|---|---|---|---|---|
| glutaminase | *E. coli* | $4 \times 10^{-4}$ M at pH 5.0 | 5.00 | 1265 at pH 5.0 |
| glutamate oxidase | Streptomyces species X-199-6 | $2 \times 10^{-4}$ M at pH 7.4 | 7.4 | ~1950 at pH 7.5 |

Figure 2:
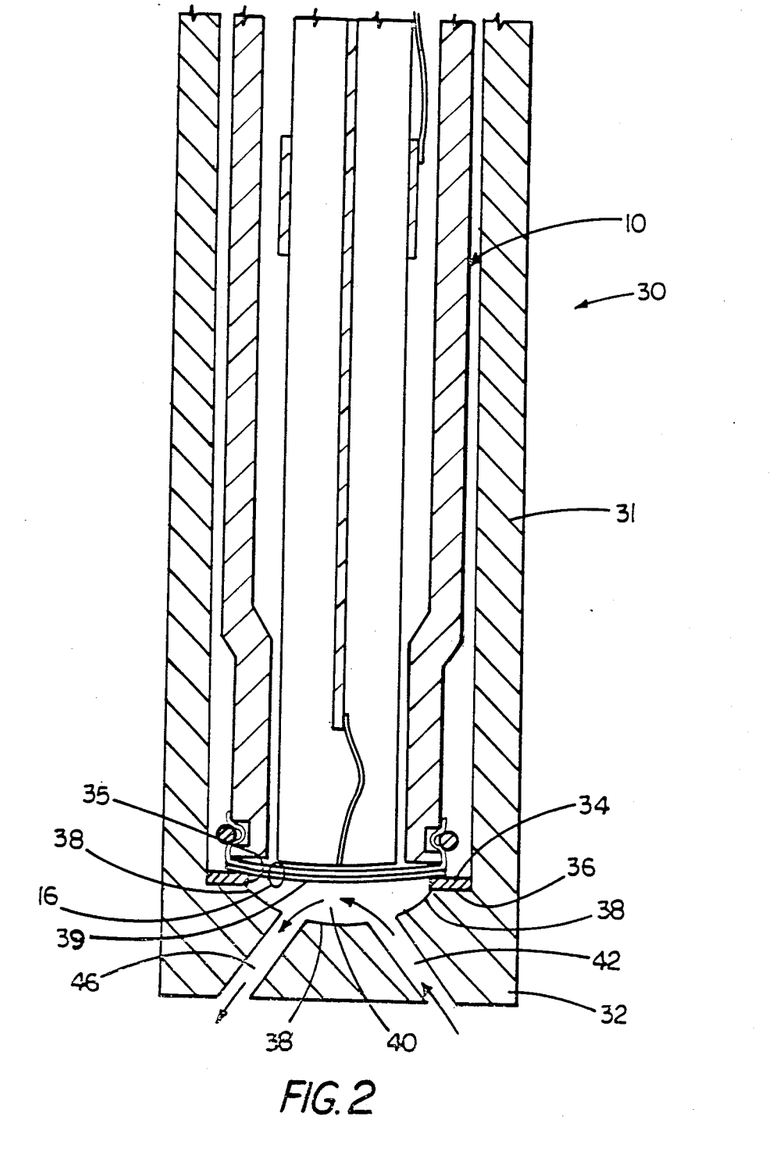
FIG. 2 is a somewhat diagrammatic sectional view of part of an L-glutamine measurement cell including said sensor.

Any suitable means may be employed for bringing a sample of the medium to be tested into contact with the enzyme-gelatin support layer. In one approach which has proven useful, the L-glutamine sensor is installed in a measurement cell, as shown in FIG. 2, and the measurement cell is connected to an auto-analyzer (Enzymat: Seres Co., Aix en Provence, France, model S 652). The successful runs which are presented below by way of example, and the data produced by them, were performed using such a measurement cell in such an auto analyzer.

With reference to FIG. 2, a measurement cell includes an L-glutamine sensor 10, as in FIG. 1, inserted into a container 30 having a container wall 31 including a sample conducting portion 32. Sensor 10 is inserted into container 30 such that bioselective membrane 16 is seated upon annular seal 34, which is seated upon shoulder 36 of sample-conducting portion 32 of container wall 31. When sensor 10 is thus seated and a seal is thus formed, a sample space 40 is defined by surface 39 of bioselective membrane 16, inner surface 35 of annular seal 34, and inner surface 38 of sample conducting portion 32 of container 31. A sample flows via inlet channel 42 into sample space 40, where it contacts surface 19 of bioselective membrane 16, and then it flows out of sample space 40 via outlet channel 46.

The measurement cycle, requiring an overall measurement time of 2 minutes per sample, includes three phases: (1) injection of the sample into the measurement cell, (2) rinsing with acetate buffer 0.1M, pH 5.5, and (3) flushing with air. These steps may be performed manually, or they may be automated.

The $O_2$ concentration within the enzyme protein matrix layer is much higher than that in the growth medium. During the measurement step the oxygen from the support is consumed first, so that the reaction rate is independent of the sample oxygen content. Because replenishing the membrane with oxygen by rinsing it with an oxygenated aqueous solution would take much longer, the membrane is flushed with air to allow a rapid recovery of the initial oxygen level.

Successful assays using the measurement cell of the invention have been performed in pure calf serum (glutamine concentration: 2 mM) and in glutamine supplemented DMEM that has been cycled through a mammalian cell culture fermenter (glutamine concentration ranging from 2.0 mM to 0.5 mM).

DEMONSTRATION OF THE L-GLUTAMINE SENSOR

1. Determination of L-Glutamine Concentration

Figure 3:
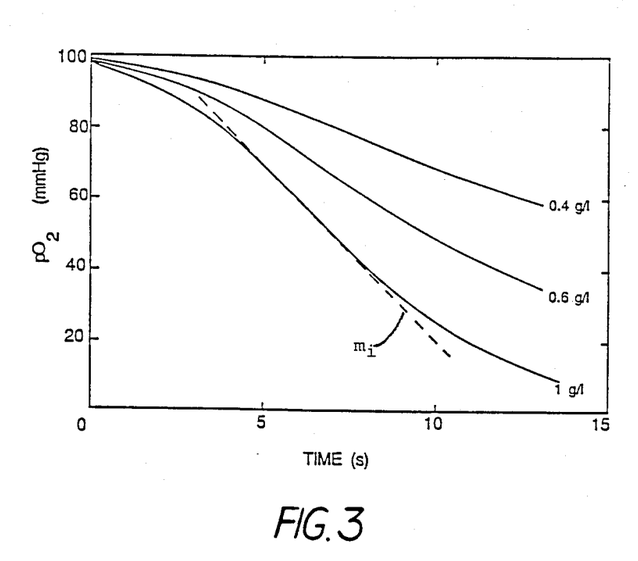
FIG. 3 is a graph showing typical responses of an L-glutamine sensor of the invention at various L-glutamine concentrations.

Biosensor responses to various sample glutamine concentrations (0.4 g/l, 0.6 g/l, 1.0 g/l) in a successful series of runs are shown in FIG. 3. The glutamine concentration can be determined by measuring the slope of the curve at the inflection point of the signal, shown for the curve from the 1.0 g/l sample by the broken line $m_i$, as described in J. P. Kernevez et al., 1983, *Biotech. Bioeng.*, vol. XXV, pages 845-55. This dynamic state treatment allows a short response time and minimizes rinsing steps.

2. Stability

Figure 4:
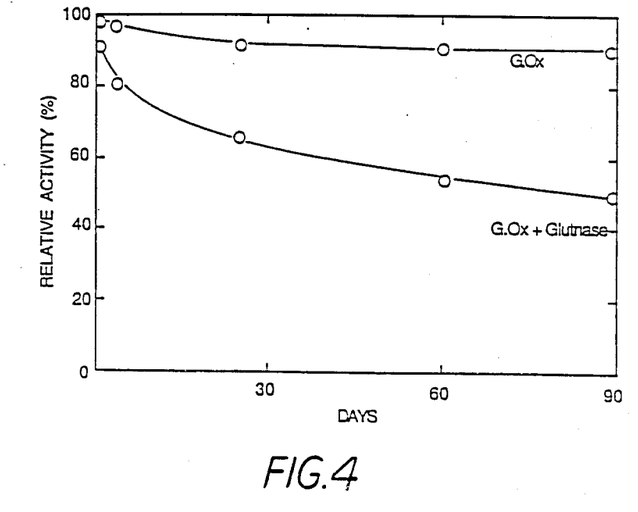
FIG. 4 is a graph showing the stability of said sensor under storage conditions.

The stability of the sensor was examined under both storage and operational conditions. When stored at 5° C. in acetate buffer 0.1 M, pH 5.5, with $10^{-4}$M sodium azide, the enzyme activities decreased as shown in FIG. 4. The activity of the glutamine-glutamate oxidase couple (FIG. 4: G.Ox+Glutnase) had fallen to fifty percent of its initial value after 3 months. Apparently, this decrease was owing mainly to the instability of the glutaminase, inasmuch as only 10% of the activity of glutamate oxidase (FIG. 4: G.Ox) had been lost in this period. Still, stability of glutaminase in this system is much better than reported from the literature (e.g., M. A. Arnold et al., *Anal. Chem.*, 1980, vol. 52, pages 1170-74), so evidently the inert protein support used to immobilize the enzymes enhanced their stabilities.

Figure 5:
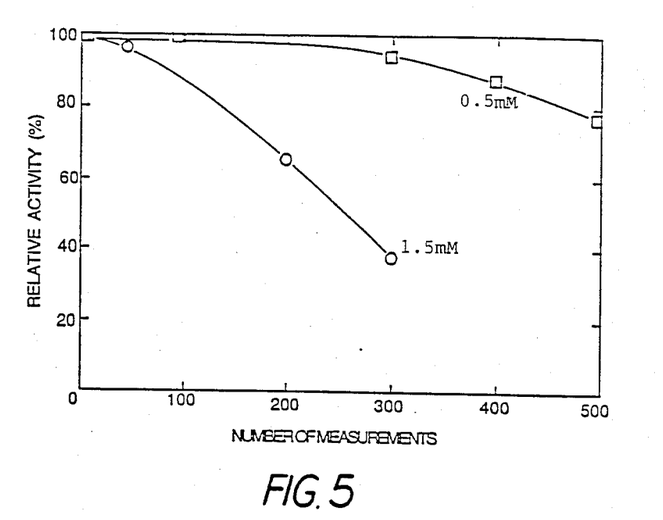
FIG. 5 is a graph showing the stability of said sensor under operating conditions.
Figure 6:
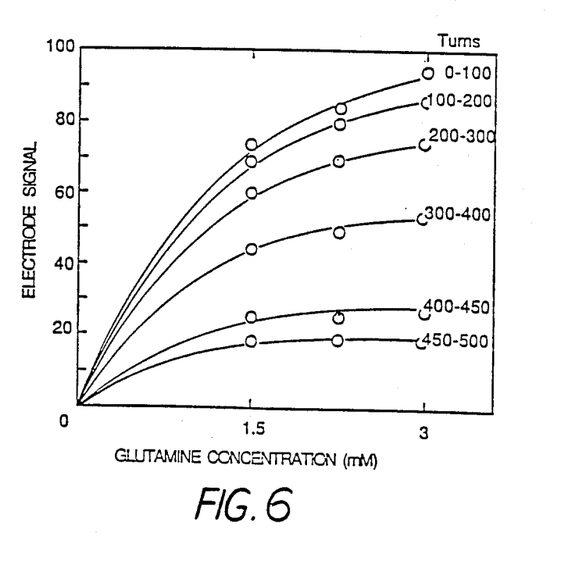
FIG. 6 ia a series of calibration curves for said sensor after progressively greater numbers of assays.

The operational stability of the sensor with repeated measurements was examined at two concentrations of glutamine (0.5 mM, 1.5 mM), and the results are shown in FIG. 5. FIG. 6 shows a family of curves for calibrations of a single biosensor after progressively greater numbers of assays (FIG. 6: Turns), illustrating the evolution of the calibration curve in use.

3. Selectivity

The selectivity of the sensor is shown in Table 2. Because the measurement cell is responsive to glutamate, glutamate contained in a sample may interfere with glutamine measurement. Glutamine may be determined in a sample containing glutamate by taking one measurement using a measurement cell as described above, having both glutaminase and glutamate oxidase immobilized in the bioselective membrane, and taking another measurement using a similar measurement cell having glutamate oxidase but not glutaminase, and then determining glutamine from the difference between the measurements.

TABLE 2

| Selectivity of the Sensor | |
| --- | --- |
| | Relative activity |
| glutamine | 75% |
| γ-glutamyl methylamide | <0.1 |
| γ-ethyl glutamate | <0.1 |
| L glutamate | 100% |
| all other L amino acids | 0 |
| D glutamate | 0 |

Figure 7:
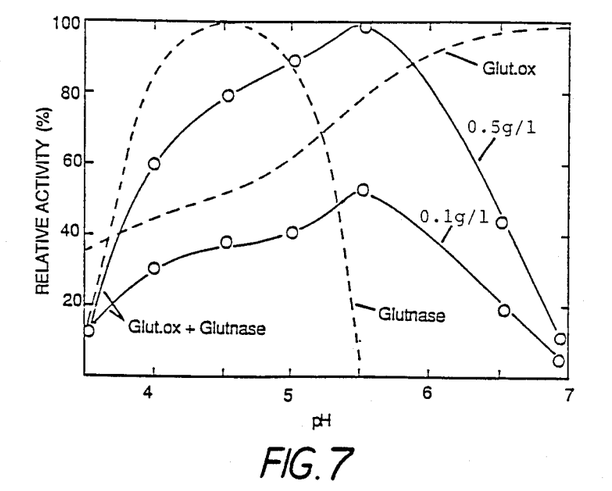
FIG. 7 is a graph showing the dependence of the activity of said sensor on pH.

As shown in FIG. 7. and also in Table 1, supra, the pH optimum for glutamate oxidase (FIG. 7: Glut.ox) is pH 7.4, while the pH optimum for glutaminase (FIG. 7: Glutnase) is pH 5.0, and glutaminase is completely deactivated above pH 5.8. Because the overall coupled enxyme reaction produces an L-ketoacid, which is retained inside the enzyme support, and because of the diffusion effect, the pH within the enzyme protein matrix layer is lower than the ordinary pH of culture media. Thus this immobilized coupled glutaminase-glutamate oxidase reaction can be used to measure glutamine concentration in culture media or other liquid samples having a pH value up to 6.5, much higher than the pH above which glutaminase is deactivated (FIG. 7: Glut.ox+Glutnase; sample glutamine concentrations 0.5 g/l and 0.1 g/l).

Figure 8:
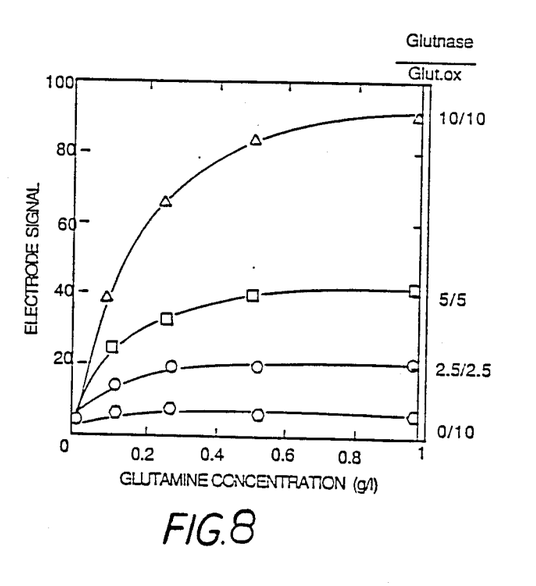
FIG. 8 is a series of calibration curves for said sensor at various ratios of concentrations of glutaminase and glutamate oxidase.

The proportions of glutaminase and glutamate oxidase immobilized in the bioselective membrane may be varied. Calibration curves of the biosensor for various ratios of concentrations of glutaminase and glutamate oxidase are given in FIG. 8.

Other embodiments are within the following claims. For example, the electrode may be one other than an oxygen electrode, such as, for example, a $H_2O_2$ electrode, and the course of the reaction may be followed by measuring some variable other than declining $O_2$ concentration, such as, for example $H_2O_2$ production. The inert protein matrix may be some proteinaceous material other than gelatin, such as, for example, bovine serum albumin, human serum albumin, or hemoglobin; or it may be a glycoprotein, such as, for example, agaragar. The inert protein matrix may alternatively be "microorganism protein", produced by homogenizing or otherwise disrupting microorganisms and insolubilizing the protein with, for example, glutaraldehyde.

We claim:
1. Apparatus for measuring L-glutamine in a liquid sample, comprising a membrane on which are immobilized the enzymes glutaminase and glutamate oxidase, whereby any said L-glutamine in said sample is acted upon by said glutaminase to form glutamic acid,. said glutamic acid being acted upon by said glutamate oxidase to form an enzymatic reaction product, said membrane being operatively associated with a sensor capable of sensing said enzymatic reaction product or a compound or element consumed or liberated in the formation or degradation thereof.

2. The apparatus of claim 1 wherein said glutaminase and said glutamine oxidase are immobilized in an insolubilized protein containing matrix.

3. The apparatus of claim 1 wherein said sensor measures dissolved oxygen and said membrane is oxygen permeable.

4. The sensor of claim 2 wherein said insolubilized protein matrix comprises gelatin.

* * * * *

UNITED STATES PATENT AND TRADEMARK OFFICE
CERTIFICATE OF CORRECTION

PATENT NO. : 4,780,191

DATED : October 25, 1988

INVENTOR(S) : Jean L. Romette et al.

It is certified that error appears in the above-identified patent and that said Letters Patent are hereby corrected as shown below:

Column 1, line 13, "on line" should be --on-line--.

Column 1, line 32, "on line" should be --on-line--.

Column 2, line 49, "Clark-type" should be --Clark type--.

Column 3, line 20, "Streptomyces" should be --Streptomyces--.

Column 4, line 13, "Streptomyces" should be --Streptomyces--.

Column 4, line 19, "ping pong" should be --ping-pong--.

Column 4, line 62, "auto analyzer" should be --auto-analyzer--.

Column 4, line 66, "sample conducting" should be --sample-conducting--.

Column 5, line 5, "sample conducting" should be --sample-conducting--.

UNITED STATES PATENT AND TRADEMARK OFFICE
CERTIFICATE OF CORRECTION

PATENT NO. : 4,780,191

DATED : October 25, 1988

INVENTOR(S) : Jean L. Romette, et al.

It is certified that error appears in the above-identified patent and that said Letters Patent is hereby corrected as shown below:

```
Column 5, line 16, "enzyme protein" should be
--enzyme-protein--.
Column 5, line 27, "glutamine supple-" should be
-- glutamine-supple- --
Column 6, line 26, "supra" should be --supra--.
Column 6, line 35, "enzyme protein" should be
--enzyme-protein--.
```

Signed and Sealed this

Seventh Day of March, 1989

Attest:

DONALD J. QUIGG

Attesting Officer

Commissioner of Patents and Trademarks